(12) United States Patent
Oosawa et al.

(10) Patent No.: US 8,189,883 B2
(45) Date of Patent: May 29, 2012

(54) SIMILAR CASE SEARCH APPARATUS AND METHOD, AND RECORDING MEDIUM STORING PROGRAM THEREFOR

(75) Inventors: Akira Oosawa, Minato-ku (JP); Hiroshi Hiramatsu, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 1122 days.

(21) Appl. No.: 12/041,179

(22) Filed: Mar. 3, 2008

(65) Prior Publication Data

US 2008/0212856 A1 Sep. 4, 2008

(30) Foreign Application Priority Data

Mar. 2, 2007 (JP) ................................ 2007-053294

(51) Int. Cl.
*G06K 9/00* (2006.01)
(52) U.S. Cl. ...................................... 382/128; 382/305
(58) Field of Classification Search .................... 382/128
See application file for complete search history.

(56) References Cited

U.S. PATENT DOCUMENTS

| | | | | |
|---|---|---|---|---|
| 5,781,899 A * | 7/1998 | Hirata | ............................ | 382/305 |
| 6,574,629 B1 * | 6/2003 | Cooke et al. | ............................ | 1/1 |
| 6,574,742 B1 * | 6/2003 | Jamroga et al. | ............... | 713/400 |
| 7,324,660 B2 * | 1/2008 | Oosawa | ......................... | 382/100 |
| 2002/0048054 A1 * | 4/2002 | Ohata et al. | .................... | 358/500 |
| 2002/0087503 A1 * | 7/2002 | Judd et al. | ........................... | 707/1 |
| 2003/0126148 A1 * | 7/2003 | Gropper et al. | .............. | 707/100 |
| 2003/0156765 A1 * | 8/2003 | Yamamichi | .................... | 382/305 |
| 2003/0174872 A1 * | 9/2003 | Chalana et al. | ............... | 382/128 |
| 2004/0003001 A1 * | 1/2004 | Shimura | .................... | 707/104.1 |
| 2004/0122790 A1 * | 6/2004 | Walker et al. | ..................... | 707/1 |
| 2005/0143646 A1 * | 6/2005 | Judd et al. | ..................... | 600/407 |
| 2007/0055699 A1 * | 3/2007 | Kasai | .......................... | 707/104.1 |
| 2008/0201372 A1 * | 8/2008 | Fukatsu et al. | ............. | 707/104.1 |
| 2008/0212856 A1 * | 9/2008 | Oosawa et al. | ............... | 382/128 |

(Continued)

FOREIGN PATENT DOCUMENTS

JP 2004-173748 A 6/2004

(Continued)

OTHER PUBLICATIONS

Lehmann TM, Wein B, Dahmen J, Bredno J, Vogelsang F, Kohnen M: Content-based image retrieval in medical applications: A novel multi-step approach. Proceedings SPIE 2000; 3972: 312-320.*

(Continued)

*Primary Examiner* — Jason M Repko
*Assistant Examiner* — Gandhi Thirugnanam
(74) *Attorney, Agent, or Firm* — Sughrue Mion, PLLC

(57) ABSTRACT

More accurate search for similar cases can be carried out in the case where images at different time phases exist. A contrast enhancement information analysis unit obtains time phase information of search target images obtained at different time phases in the same examination from accompanying information of the images, and a similar case database storing similar case information sets each including examination ID, time phase information, a characteristic quantity, and image interpretation/diagnosis support information is searched in processing by a first similar case information search unit, a second similar case information search unit, and a judgment unit. A corresponding portion of the similar case information sets satisfying three conditions comprising agreement of the time phase information with the search target images, agreement of examination between the portion of the similar case information sets, and similarity of a content-based characteristic to the search target images is obtained.

11 Claims, 7 Drawing Sheets

U.S. PATENT DOCUMENTS

| | | | |
|---|---|---|---|
| 2008/0215630 A1* | 9/2008 | Oosawa et al. | 707/104.1 |
| 2008/0240494 A1* | 10/2008 | Oosawa et al. | 382/100 |
| 2008/0243886 A1* | 10/2008 | Oosawa et al. | 707/100 |
| 2008/0253628 A1* | 10/2008 | Matsue et al. | 382/128 |
| 2008/0253629 A1* | 10/2008 | Kazuno et al. | 382/128 |
| 2008/0317309 A1* | 12/2008 | Kazuno et al. | 382/128 |
| 2010/0128943 A1* | 5/2010 | Matsue et al. | 382/128 |
| 2010/0228727 A1* | 9/2010 | Hisanaga et al. | 707/723 |
| 2010/0232661 A1* | 9/2010 | Hisanaga et al. | 382/128 |

FOREIGN PATENT DOCUMENTS

| | | |
|---|---|---|
| JP | 2005-198887 A | 7/2005 |
| JP | 2005-246032 A | 9/2005 |

OTHER PUBLICATIONS

T.F. Cootes et al., Active Appearance Models, European Conference on Computer Vision, 1998, pp. 484-498, vol. 2.

\* cited by examiner

FIG.5A
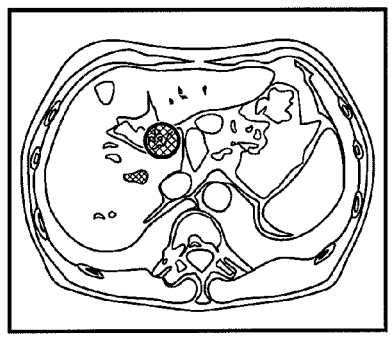
FIG.5B
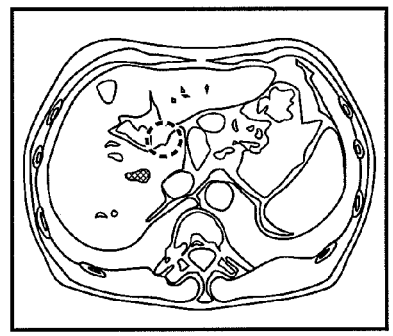
FIG.6
| EXAMINATION ID | Pa (TO $I_1$) | Pb (TO $I_2$) | PRIORITY |
|---|---|---|---|
| 001 | SIMILAR | SIMILAR | 1 |
| 002 | SIMILAR | DISSIMILAR | 4 |
| 003 | SIMILAR | NO MATCH FOR PHASE | 2 |
| 004 | SIMILAR | NO MATCH FOR EXAMINATION | 3 |

FIG.8

| EXAMINATION ID | PHASE | | | |
|---|---|---|---|---|
| | Pa | Pb | Pc | Pd |
| 001 | ○ | ○ | ○ | ○ |
| 002 | ○ | ○ | ○ | ○ |
| 003 | ○ | × | ○ | ○ |
| 004 | ○ | × | × | × |

SIMILAR CASE SEARCH APPARATUS AND METHOD, AND RECORDING MEDIUM STORING PROGRAM THEREFOR

BACKGROUND OF THE INVENTION

1. Field of the Invention

The present invention relates to an apparatus and a method for searching for information of cases similar to a search target medical image, and to a recording medium, in which a program causing a computer to execute the method is recorded.

2. Description of the Related Art

In order to support interpretation of medical images by physicians and diagnosis carried out by clinicians based on medical images, similar case search systems have been proposed. In such systems, medical images, information including interpretation results and diagnosis results pertinent to the images, and the like are stored in databases, and the databases are searched for images similar to medical images as targets of image interpretation/diagnosis and for information such as results of image interpretation/diagnosis pertinent to the similar images.

For example, a system is known wherein an image database storing image data sets representing images of subjects is searched for similar image data sets having regions whose pictorial characteristic is similar to an image data set inputted as a search target and a result of the search is outputted (see U.S. Patent Application Publication No. 20040003001, for example).

In addition, a similar medical image search apparatus having a similar medical image database is known (see Japanese Unexamined Patent Publication No. 2004-173748, for example). The similar medical image database relates to each other the types of operations for judgment processing used at the time of detection of shadows of foci included in medical images, a characteristic quantity of the shadows of foci found in the judgment processing, and the medical images. The similar medical image search apparatus searches the similar medical image database based on a result of the same judgment processing carried out on one of a plurality of interpretation target images.

In medical imaging, lesions are identified in many cases by obtaining temporal change images of the same body part associated with infusion of a contrast material, that is, images at different times. For example, in the case of examination to identify a liver tumor by use of CT, difference in spread of a contrast material is observed between images of four temporal changes comprising a pre-contrast phase image (plain CT), an early phase image (an arterial phase image), a portal phase image (a portal venous phase image), and a late phase image (an equilibrium phase image), and judgment is made on distinction between veins and the tumor and on progress of the disease.

A region of liver tumor has small differences in CT values from other normal liver regions. In addition, the region in an image obtained at a single time phase is sometimes extracted as a region similar to surrounding veins, depending on how a contrast material has spread. Therefore, a plurality of images at different time phases need to be obtained for comparison of complex changes associated with temporal changes in an amount of absorbed X rays, that is, complex changes in CT values with time.

In the case where the similar case search system or the like described in U.S. Patent Application Publication No. 20040003001 or Japanese Unexamined Patent Publication No. 2004-173748 is applied to identification of such a liver tumor, not all temporal change images described above are used, since the system searches for similar cases by using only one image as a search target.

Furthermore, the system does not maximally use information obtained in examinations, and whether images to be compared to each other were obtained at the same time phase has not been considered.

SUMMARY OF THE INVENTION

The present invention has been conceived based on consideration of the above circumstances, and an object of the present invention is to provide an apparatus, a method, and a recording medium storing a program that can achieve higher accuracy in a search for a similar case in the case where images at different time phases exist.

A similar case search apparatus of the present invention comprises:

a similar case database storing similar case information sets each including: examination identification information that identifies an examination for obtaining a medical image; time phase information representing each of time phases in the case where a plurality of medical images at the respective time phases are obtained in the examination; characteristic information representing a content-based characteristic of at least a region in the medical image; and image interpretation/diagnosis support information for supporting interpretation of a medical image whose content-based characteristic is similar thereto and/or for supporting diagnosis based on the medical image having the similar content-based characteristic, while relating the time phase information of each of the time phases to the examination identification information in each of the similar case information sets and relating the characteristic information in each of the similar case information sets to the time phase information of each of the time phases;

time phase information acquisition means for obtaining information representing different time phases of a plurality of search target images obtained at the time phases in one and the same examination from accompanying information added to the respective search target images; and similar case search means for carrying out a search of the similar case database for at least the image interpretation/diagnosis support information in a corresponding portion of the similar case information sets that satisfies all of search conditions comprising: a first search condition that the time phase information representing the respective time phases of the search target images exists; a second search condition that the time phase information representing the respective time phases is related to the examination identification information representing one and the same examination; and a third search condition that the characteristic information related to the time phase information representing each of the time phases represents similarity in the content-based characteristic to at least a region in a corresponding one of the search target images at the corresponding time phase.

A similar case search method of the present invention comprises the steps of:

obtaining information representing different time phases of a plurality of search target images obtained at the respective time phases in one and the same examination from accompanying information added to the respective search target images; and searching a similar case database storing similar case information sets each including: examination identification information that identifies an examination for obtaining a medical image; time phase information representing each of time phases in the case where a plurality of medical images at the respective time phases are obtained in the examination; characteristic information representing a content-based characteristic of at least a region in the medical image; and image interpretation/diagnosis support information for supporting interpretation of a medical image whose content-based characteristic is similar thereto and/or for supporting diagnosis based on the medical image having the similar content-based characteristic while relating the time phase information of each of the time phases to the examination identification information in each of the similar case information sets and relating the characteristic information in each of the similar case information sets to the time phase information of each of the time phases. The step of searching is the step of searching the database for at least the image interpretation/diagnosis support information in a corresponding portion of the similar case information sets that satisfies all of search conditions comprising: a first search condition that the time phase information representing the respective time phases of the search target images exists; a second search condition that the time phase information representing the respective time phases is related to the examination identification information representing one and the same examination; and a third search condition that the characteristic information related to the time phase information representing each of the time phases represents similarity in the content-based characteristic to at least a region in a corresponding one of the search target images at the corresponding time phase.

A recording medium storing a similar case search program of the present invention stores a program that causes a computer to execute the method described above.

Hereinafter, the present invention will be described in detail.

The "examination" refers to imaging by one type of examination modality.

The "medical images" refer to images representing a predetermined body part of a subject as an examination target obtained by an examination modality such as CT or MRI. More specifically, the medical images refer to slice images of abdomen (liver) of a human body obtained by CT.

The case where images representing temporal changes in an examination target body part associated with infusion of a contrast material are obtained can be listed as an example of the case where "a plurality of medical images at the respective time phases were obtained in the examination". More specifically, the case refers to the case where four images are obtained representing a pre-contrast phase image, an early phase image, a portal phase image, and a late phase image in an examination of liver tumor, for example.

The "time phase information" refers to each of stages of temporal changes, such as a pre-contrast phase, an early phase, a portal phase, and a late phase. Description of series as a portion of the accompanying information of the medical images may be used as the time phase information. Alternatively, in the case where the time elapsed after infusion of a contrast material is added to the images, the time phases may be assigned to the images based on the elapsed time.

A region of interest is listed as "at least a region in the medical image". The region of interest is a region to which attention is paid at the time of image interpretation and diagnosis, and a characteristic thereof greatly affects diagnosis. The region of interest is generally referred to as ROI (Region Of Interest). The region of interest may be a region specified by an observer of the medical image displayed on a screen with a pointing device or the like, or detected by a known image analysis method for detecting a region of abnormal shadow in a medical image. Alternatively, the region of interest may be a region determined by combination of manual specification and detection, such as a region specified by the observer and an outline of which is extracted by the detection method, or a region detected by the method and selected by the observer. The region of interest in a second search target image that is different from a first search target image may be automatically determined at a position corresponding to the region of interest determined in the first search target image.

The "content-based characteristic" refers to a characteristic related to the content of the medical image. More specifically, the content-based characteristic refers to a characteristic of luminance, an edge, a shape, a size, or an isolated region, for example. The content-based characteristic may be a combination of a plurality of types of characteristics.

"Representing a content-based characteristic of at least a region in the medical image" refers to a content-based characteristic of the region such as a region of interest in the medical image, or a content-based characteristic of the entire image, or a content-based characteristic of the region and of the entire image, or a combination of a content-based characteristic of the region and a content-based characteristic of a remaining region.

A characteristic quantity that quantifies the content-based characteristic may be an example of the "characteristic information". The characteristic quantity can be obtained by a known image analysis method. The characteristic information may be image data themselves.

An image interpretation report of the medical image generated by a radiologist or the like or finally confirmed diagnosis information on the examination target body part in the medical image may be listed as an example of the "image interpretation/diagnosis support information". Alternatively, the image interpretation/diagnosis support information may be the medical image itself representing the examination target body part. Hereinafter, each of the examples will be described below in detail.

The image interpretation report or the finally confirmed diagnosis information may be generated based on image interpretation information and/or diagnosis information obtained from storage means that stores the image interpretation information representing a result of image interpretation of the medical image of the subject and/or the diagnosis information representing the content of diagnosis of the subject while relating the image interpretation information and/or the diagnosis information to the medical image of the subject.

A database that stores image interpretation reports, electronic charts, and the like and comprises a medical information management system such as a Radiology Information System (RIS), a Picture Archive and Communication System (PACS), or a Hospital Information System (HIS) may be listed as an example of the storage means.

Storing the image interpretation information and/or the diagnosis information by relating the image interpretation information and/or the diagnosis information to the medical image refers to storing the image interpretation information and/or the diagnosis information in a state where a portion of either the image interpretation information and/or the diagnosis information or the medical image allows direct or indirect access to the other. As an example of direct access, the case may be listed where the image interpretation information has a report ID that identifies the image interpretation information itself and an image ID that identifies the medical image having been interpreted while the medical image has the image ID that identifies the image itself and the report ID that identifies the image interpretation report of the image. In this case, the image interpretation information allows direct access to the medical image based on the image ID while the medical image allows direct access to the image interpretation information based on the report ID. As an example of indirect access, the following case may be listed. The diagnosis information has a examination ID that identifies the diagnosis information and an examination ID that identifies an examination carried out on the patient while the medical image has an image ID that identifies the image itself and the examination ID that identifies the examination including imaging of the medical image. In addition, examination information including the examination ID that identifies the examination, the examination ID that identifies the patient having been subjected to the examination, and the image ID that identifies the image obtained in the examination exists. In this case, the diagnosis information allows indirect access to the medical image by identifying the examination information according to the examination ID and by identifying the image obtained in the examination according to the image ID included in the examination information. The medical image also allows indirect access to the diagnosis information by identifying the examination information according to the examination ID and by identifying the diagnosis information based on the examination ID included in the examination information.

The "storage means" does not need to store the medical image related to the image interpretation information and/or the diagnosis information.

The "image interpretation information" may be an image interpretation report describing an image interpretation result by a plurality of radiologists. The "diagnosis information" can include not only the finally confirmed diagnosis information and a remark based on the corresponding medical image but also all information that can be obtained during a diagnosis process of the subject, such as a result of another examination or health interview, and the content of treatment.

The image interpretation/diagnosis support information may be generated based on the image interpretation information and/or the diagnosis information by extraction of predetermined information from the image interpretation information and/or the diagnosis information or by using the image interpretation information and/or the diagnosis information as the image interpretation/diagnosis support information.

The "image interpretation/diagnosis support information" may be link information to a location of storage of the content thereof. More specifically, the image interpretation/diagnosis support information may be the name of a database that stores the image interpretation report of the medical image, an electronic chart of the subject, and the medical image itself, and search key information for obtaining information from the database.

The "examination identification information" and the "time phase information" included in each of the similar case information sets in the similar case database may be defined as items of the database (a table). Alternatively, like the search target images, the examination identification information and the time phase information may be a portion of the "characteristic information" or the "image interpretation/diagnosis support information", attached to the medical images stored in the database. The method by which the examination identification information and the time phase information are attached to the medical images is the same as that for the search target images.

As a method of adding the "accompanying information" to the medical image, a method according to the DICOM standard may be listed. In the DICOM standard, the "examination identification information" is added as general examination information, and the "time phase information" is added as a series description, positional relation information in series, or contrast material information, for example.

As an example of judgment according to the "third search condition" as to whether "the characteristic information related to the time phase information representing each of the time phases represents similarity in the content-based characteristic to at least a region in a corresponding one of the search target images at the corresponding time phase", judgment processing according to a criterion may be used. The criterion may be that a difference of the characteristic quantity in at least a region in the search target image from the characteristic information (the characteristic quantity) in the corresponding similar case information set is minimal, or a predetermined threshold value or smaller. Alternatively, the criterion may be that up to a predetermined number of the similar case information sets are extracted in order of smaller difference of the characteristic quantity, for example.

As a specific method of the search according to the first to third search conditions, the following method may be used. The method comprises the steps of:

obtaining a corresponding portion of the similar case information sets having the time phase information representing the time phase of a first search target image as one of the search target images and representing that the characteristic information related to the time phase information thereof shows similarity in the content-based characteristic to at least a region in the first search target image; and extracting a corresponding portion of the similar case information sets having the time phase information representing the time phase of a second search target image different from the first search target image and showing similarity in the content-based characteristic in the characteristic information related to the time phase information to at least a region in the second search target image, from a corresponding portion of the similar case information sets having the examination identification information representing the same examination as the portion of the similar case information sets having been obtained.

When judgment is made on the similarity of the content-based characteristic to at least a region in the second search target image, a corresponding portion of the similar case information sets representing that a difference in the characteristic information between the respective time phases thereof is similar to a difference in the content-based characteristic of at least a region between the first and second search target images may be extracted from within a corresponding portion of the similar case information sets having the examination identification information representing the same examination and having the time phase information representing the time phases of the first and second search target images. In this case, the difference in the content-based characteristic between the medical images at the different time phases in one and the same examination may have been registered as the characteristic information of a corresponding portion of the similar case information sets in the similar case database.

Upon judgment on a degree of conformity with the first to third search conditions described above, the degree of conformity may be lowered in the following order:

(1) the case where a corresponding portion of the similar case information sets satisfying all the first to third search conditions exists for all the search target images;

(2) the case where a corresponding portion of the similar case information sets satisfying all the first to third search conditions exists for a portion of the search target images but a corresponding portion of the similar case information sets satisfying the first or second search condition does not exist for the remaining portion of the search target images;

(3) the case where a corresponding portion of the similar case information sets satisfying all the first to third search conditions exists for a portion of the search target images but a corresponding portion of the similar case information sets satisfying the third search condition does not exist for the remaining portion of the search target images although a corresponding portion of the similar case information sets satisfying the first or second search condition exists for the remaining portion of the search target images.

Moreover, examination identification information that identifies the examination in which the first search target image as one of the search target images was obtained and the information representing the time phase of the first search target image may be obtained from the accompanying information of the first search target image so that a medical image having the accompanying information including the examination identification information representing that the medical image was obtained in the same examination as the first search target image and including the information representing the time phase different from the first search target image can be obtained as the second search target image.

The similar case search apparatus of the present invention may further comprise means for outputting the portion of the similar case information sets having been obtained in the search. More specifically, the portion of the similar case information sets may be outputted as display on a display screen, or by printing, or as electronic data in a recording medium of the search apparatus. The content of the output may be all the portion of the similar case information sets, or a portion thereof. Alternatively, in the case where the portion of the similar case information sets was not found through the search, the content of the output may be information representing the fact.

By execution of the similar case search of the present invention, the time phase information of each of the search target images obtained at the respective time phases in the same examination is obtained from the accompanying information of the images. The similar case database storing the similar case information sets each having the examination identification information, the time phase information, the characteristic information, and the image interpretation/diagnosis support information is then searched for the portion of the similar case information sets satisfying all the search conditions comprising the first search condition that the time phase information representing the time phases of the search target images exists, the second search condition that the time phase information representing the time phases of the search target images is related to the examination identification information representing one and the same examination, and the third search condition that the characteristic information related to the time phase information representing the time phases shows similarity in the content-based characteristic to at least a region in the search target images of the corresponding time phases. In other words, the similar case database is searched by using the images obtained at the different time phases in the same examination as the search target images, and the portion of the similar case information sets satisfying the three search conditions, that is, agreement of the time phases to the search target images, agreement of the examination therein, and similarity in the content-based characteristic to the search target images is obtained. Therefore, by effectively using the images at the different time phases in the same examination, which have not been used conventionally, accuracy improves in the similar case search. Consequently, this improvement contributes to reduction in errors in judgment at the time of image interpretation or diagnosis, such as erroneous judgment caused by incapability to detect a difference between veins and a lesion.

In the case where the search according to the first to third search conditions comprises the steps of: obtaining the portion of the similar case information sets whose time phase information is the same as the first search target image and whose characteristic information related to the time phase information representing the time phase is similar in the content-based characteristic to at least a region in the first search target image; and extracting the portion of the similar case information sets whose time phase information is the same as the second search target image and whose characteristic information related to the time phase information representing the time phase is similar in the content-based characteristic to at least a region in the second search target image from the portion of the similar case information sets having the same examination identification information as the portion of the similar case information sets having been obtained, a portion of the similar case information sets whose similarity in the content-based characteristic to the second search target image is judged is limited to a corresponding portion of the similar case information sets obtained in the same examination as the portion of the similar case information sets satisfying the conditions of agreement of the time phase and similarity in the content-based characteristic to the first search target image. Therefore, the number of times of processing to judge the similarity in the content-based characteristic, which imposes a heavy processing load, can be reduced. Consequently, the search processing can be faster.

Upon judgment on the similarity in the content-based characteristic to at least a region in the second search target image, in the case where the portion of the similar case information sets showing similarity in the difference of the characteristic information between the time phases thereof to the difference in the content-based characteristic of at least a region between the first and second search target images is extracted from within the portion of the similar case information sets having the examination identification information representing the same examination and having the same time phases as the first and second search target images, the similarity can be judged while reflecting a change between the corresponding medical images at the respective time phases. Consequently, accuracy of the search improves.

Upon judgment on the degree of conformity with the first to third search conditions described above, if the degree of conformity is lowered for the case where the portion of the similar case information sets satisfying all the first to third search conditions exists for a portion of the search target images although the portion of the similar case information sets satisfying the third search condition does not exist for the remaining portion of the search target images regardless of existence of the portion of the similar case information sets satisfying the first or second search condition for the remaining portion of the search target images than for the case where the corresponding portion of the similar case information sets satisfying all the first to third search conditions exists for a portion of the search target images although the corresponding portion of the similar case information sets satisfying the first or second search condition does not exist for the remaining portion of the search target images, distinction can be made between the case where the portion of the similar case information sets corresponding to the respective time phases of the search target images exists but the content-based characteristic thereof is dissimilar for a portion of the corresponding medical images and the case where a portion of the similar case information sets corresponding to a portion of the time phases of the search target images does not exist. Therefore, the degree of conformity for the former case that is not thought to be similar cases when the time elapsed in the examination is considered can be lowered than for the latter case where pictorial similarity deserves consideration although the time elapsed in the examination cannot be considered. Consequently, the more detailed similar case information sets can be provided.

If the examination identification information and the time phase information is obtained from the accompanying information of the first search target image and if the second search target image generated in the same examination as the first search target image but having a different time phase from the first search target image is obtained based on the examination identification information and the time phase information having been obtained, similar cases including the second search target image can be searched for even in the case where a medical image observer recognizes only the first search target image. Consequently, accuracy of image interpretation and diagnosis can be improved.

In the case where the characteristic quantity representing the content-based characteristic of at least a region in the corresponding medical image is registered as the characteristic information in the each of the similar case information sets instead of the medical image itself, the characteristic quantity does not need to be calculated from the image data registered as the characteristic information, in each search for similar cases. Consequently, a processing load can be reduced.

If a target of judgment on the similarity of the content-based characteristic is a region of interest in the corresponding medical image, more appropriate similar cases can be searched for by judgment on the similarity of the content-based characteristic in the important part of the image. Therefore, accuracy of image interpretation/diagnosis improves. If the region of interest in the second search target image is automatically set at the position corresponding to the region of interest in the first search target image, an image interpreter/a person who diagnoses does not need to set the region of interest therein. If the region of interest is detected automatically in each of the search target images, a burden on the interpreter/the person who diagnoses can be reduced further, and oversight of a lesion in the corresponding medical image is reduced.

If the image interpretation/diagnosis support information includes the corresponding medical image itself that is related thereto, the medical image obtained as the image interpretation/diagnosis support information can be referred to upon image interpretation of the search target images and upon diagnosis based on the search target images, which contributes to comparison and interpretation of the images.

In the case where the image interpretation/diagnosis support information is the link information to the image interpretation/diagnosis support information and to the image data stored in another medical information system such as RIS, PACS, or HIS, storage space can be saved, since the information of the same content does not need to be stored at a plurality of locations. In addition, disagreement in data content that could occur in the case where only the information stored at one of the locations has been updated can be avoided, and reliability of the information improves. Furthermore, simultaneous processing of the data to avoid such disagreement becomes unnecessary. In this manner, a processing load on the system can be reduced. The effect of avoidance of the data disagreement problem is high, since electronic chart information or the like as an example of the diagnosis information is to be updated especially.

BRIEF DESCRIPTION OF THE DRAWINGS

FIGS. 5A and 5B show examples of medical images at different contrast enhancement phases to be interpreted and used as search target images;

FIG. 6 is a block diagram showing an example of processing to judge a degree of conformity with search conditions;

FIG. 8 shows an example of an index table for the similar case database in the embodiment.

DESCRIPTION OF THE PREFERRED EMBODIMENT

Hereinafter, an embodiment of the present invention will be described with reference to the accompanying drawings.

Figure 1:
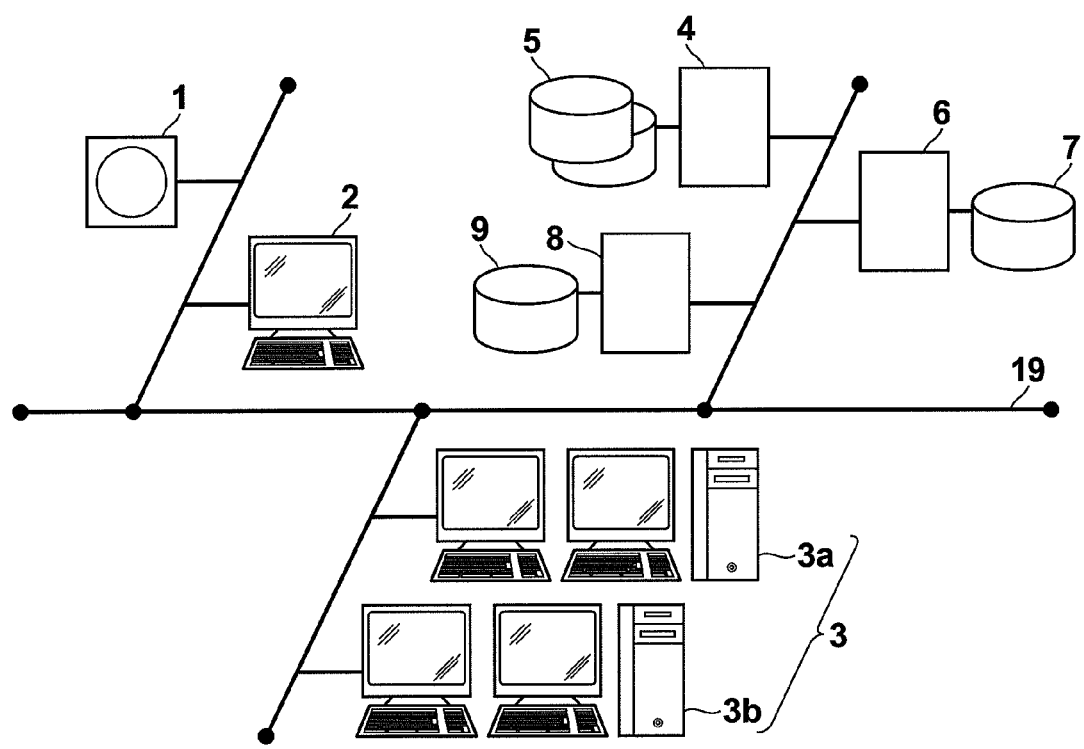
FIG. 1 shows the configuration of a medical information system to which a similar case search apparatus of an embodiment of the present invention has been introduced.

FIG. 1 shows the configuration of a medical information system to which a similar case search apparatus of a first embodiment of the present invention has been introduced. As shown in FIG. 1, the system comprises an imaging apparatus (a modality) 1 for obtaining medical images, a workstation (QA-WS) 2 for checking image quality, workstations 3 (3a and 3b) for physicians to perform imaging diagnosis (hereinafter simply referred to as the workstations 3), an image information management server 4, an image information database 5, an image interpretation report server 6, an image interpretation report database 7, a similar case search server 8, and a similar case database 9, all of which are connected in a communicable state via a network 19. Each of the apparatuses is controlled by a program installed from a recording medium such as a CD-ROM. The program may be installed after being downloaded from a server connected via a network such as the Internet.

The modality 1 includes an apparatus that generates an image data set representing a three-dimensional image of a body part of a subject by imaging the body part as an examination target. The modality 1 outputs the image data set added with accompanying information defined by the DICOM standard, as an image information set. More specifically, the modality 1 may be an apparatus of CT (Computed Tomography), MRI (Magnetic Resonance Imaging), PET (Positron Emission Tomography), or ultrasonography. The modality 1 also obtains images of temporal changes in the examination target body part associated with infusion of a contrast material, by CT or the like. The images can be search target images for the similar case search apparatus of the present invention. Hereinafter, the "image information set" refers to a combination of the image data set representing the subject and the accompanying information added thereto. In other words, the image information set includes text information regarding the medical image.

The QA-WS 2 comprises a general-purpose processor (a computer), one or two high-definition display(s), and input devices such as a mouse and a keyboard. Software, for supporting operation by a technician who is to perform examinations, is installed in the processor. According to a function realized by execution of the software, the QA-WS 2 receives the image information set according to the DICOM standard from the modality 1, and prompts the technologist to confirm the image data set included in the image information set and the content of the accompanying information therein by display of the image information set on a screen. The QA-WS 2 transfers the image information set confirmed by the technologist to the image information management server 4 via the network 19, and requests registration of the image information set with the image information database 5.

The workstations 3 are apparatuses for physicians to perform imaging diagnosis and used by the physicians to interpret the medical images and to generate image interpretation reports. Each of the workstations 3 comprises a processor, one or two high-definition display(s) (hereinafter, the display or one of the displays is referred to as the display), and input devices such as a mouse and a keyboard. The workstations 3 request image viewing from the image information management server 4, display the images received from the image information management server 4, automatically detect parts in the images which seem to be lesions and display the parts with emphasis thereon, support generation of the image interpretation reports, request registration and viewing of the image interpretation reports from the image interpretation report server 6, display the image interpretation reports received from the image interpretation report server 6, request viewing of similar case information sets from the similar case search server 8, display the similar case information sets received from the similar case search server 8, and request registration of similar case information sets from the similar case search server 8, for example.

The image information management server 4 is a general-purpose computer with comparatively high performance, and has a software program installed therein for providing functions of a database management system (DBMS). The image information management server 4 also has a large-capacity storage comprising the image information database 5. The storage may be a large-capacity hard disk connected to the image information management server 4 by a data bus, or a disk device connected to a NAS (Network Attached Storage) or SAN (Storage Area Network) connected to the network 19.

Image data sets representing images of subjects and accompanying information thereof are registered with the image information database 5. The accompanying information can include image ID for identifying each of the images, examination ID for identifying each of the subjects, examination ID for identifying an examination, unique identifier (UID) assigned for each of the image information sets, date of examination on which the corresponding image information set was generated, time of the examination, type of modality used in the examination for obtaining the image information set, patient information such as name, age, and gender of patient, examined body part (imaged body part), imaging condition (use or non-use of contrast material and time elapsed after infusion of the material/dye used in imaging, type of radionuclide, amount of radionuclide, and so on), and series number or collection number when a plurality of images were obtained in one examination, for example. The image information sets are managed as XML or GML data.

When the image information management server 4 receives a request for registration of the image information set sent from the QA-WS 2, the image information management server 4 changes the image information set into the format for the image information database, and registers the image information set with the image information database 5.

Upon reception of viewing request sent from any one of the workstations 3 (hereinafter referred to as the workstation 3) via the network 19, the image information management server 4 searches the image information sets registered with the image information database 5, and extracts a requested one of the image information sets to send the image information set to the workstation 3.

When a user such as a physician to carry out imaging diagnosis operates the workstation 3 to request viewing of one or more of the images as a target of image interpretation (hereinafter referred to as the image interpretation target image or images), the workstation 3 sends a viewing request to the image information management server 4, and obtains the corresponding image information set or sets necessary for image interpretation. The workstation 3 displays the image information set or sets on a display screen, and carries out automatic lesion detection processing or the like in response to a request of the physician.

The workstation 3 further displays a report generating screen on the display screen for supporting generation of a corresponding image interpretation report. When a radiologist inputs text representing a diagnosis (a remark and the like) based on image interpretation, the workstation 3 generates the image interpretation report that records the inputted information and the interpretation target image or images. When the number of the image interpretation target images is larger than 1, the image interpretation report records a representative one of the images (hereinafter referred to as the representative image) that influenced the diagnosis most. The workstation 3 transfers the generated image interpretation report to the image interpretation report server 6 via the network 19, and requests registration of the report with the image interpretation report database 7.

The image interpretation report server 6 is a general-purpose computer with comparatively high performance, and has a software program installed therein to provide functions of a database management system (DBMS). Upon reception of the request for registration of the image interpretation report sent from the workstation 3, the image interpretation report server 6 changes the image interpretation report into the format to fit the database, and registers the report with the image interpretation report database 7.

Information such as image ID for identifying the image interpretation target image or the representative image, image interpreter ID for identifying the physician who carried out image interpretation, position information on region of interest, remark, and certainty of the remark is registered with the image interpretation report database 7. In addition, the image interpretation report database 7 can also include examination number and patient number obtained by referring to the accompanying information of the image information set at the time of image interpretation, and an image data set itself of the image interpretation target image or the representative image. The image data set may be a copy of the image data set registered with the image information database, or a reduced image data set having a smaller number of pixels (that is, thinned data) than the image data set in the image information database 5. The image data set may be link information representing location (such as a folder) and file name of the image data set in the image information database 5, for example. The position information on the region of interest may be registered with the image information database 5 as a portion of the accompanying information of the image data set, instead of the image interpretation report database 7. The image interpretation report is managed as XML or GML data, for example.

Upon reception of a viewing request sent from the workstation 3 via the network 19, the image interpretation report server 6 searches the image interpretation reports registered with the image interpretation report database 7, and sends an extracted one of the reports to the workstation 3 requesting the report.

The similar case search server 8 is a general-purpose computer with comparatively high performance, and has a software program installed therein to provide functions of database management system (DBMS). The similar case database 9 stores the images having been interpreted and image interpretation results on the images, as the similar case information sets. The similar case search apparatus as the embodiment of the present invention is installed as a client-server system wherein the similar case search server 8 having the similar case database 9 is connected with the workstations 3 by the network 19. Details of the apparatus will be described later.

The network 19 is a local area network connecting various kinds of apparatuses in a hospital. In the case where a part of the workstations 3 is also installed in another hospital or clinic, the network 19 may connect local area networks in the respective hospitals by the Internet or a dedicated line. In either case, it is preferable for the network 19 to be an optical network or the like that can realize high-speed transfer of the image information sets.

Figure 2:
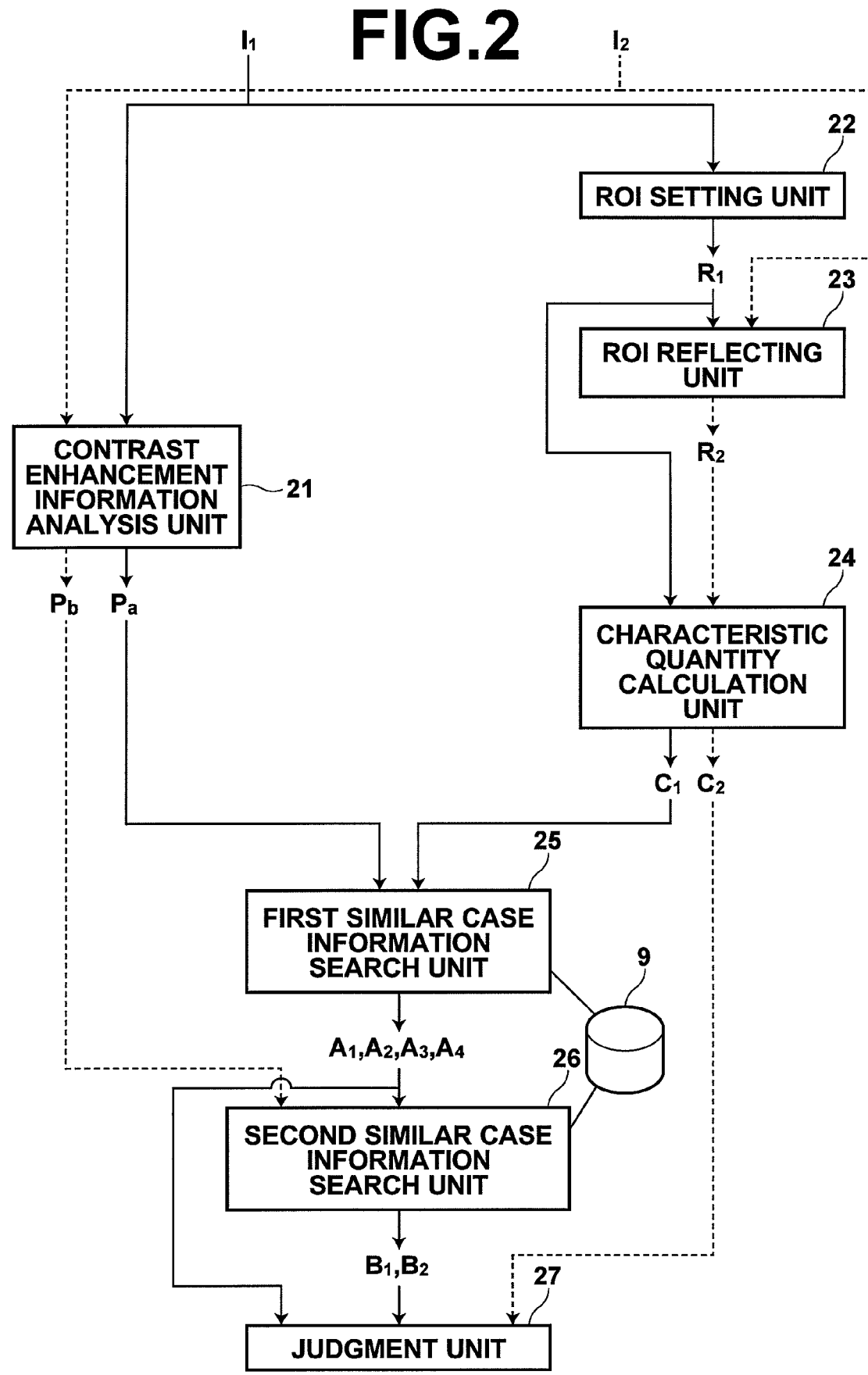
FIG. 2 is a block diagram showing the configuration of the similar case search apparatus in the embodiment.

The similar case search apparatus in the embodiment of the present invention will be described below in detail for the case as an example where the interpretation target images are four images obtained by CT and representing temporal changes in a liver associated with infusion of a contrast material. The four images represent four contrast enhancement phases (time phases), that is, at a pre-contrast phase (plain CT), an early phase (an arterial phase), a portal phase (a portal venous phase), and a late phase (an equilibrium phase). FIG. 2 is a block diagram showing the configuration of the similar case search apparatus and the flow of data therein. As shown in FIG. 2, the apparatus comprises a contrast enhancement information analysis unit 21, a unit 22 for setting a region of interest (hereinafter referred to as the ROI setting unit 22), a unit 23 for reflecting the region of interest (hereinafter referred to as the ROI reflecting unit 23), a characteristic quantity calculation unit 24, a first similar case information search unit 25, a second similar case information search unit 26, a judgment unit 27, and the similar case database 9.

The contrast enhancement information analysis unit 21 analyses series description, positional relationship information on series, and contrast material information as a portion of the accompanying information of each of the image data sets conformed to the DICOM standard having been inputted, and obtains contrast enhancement information representing any one of the four contrast enhancement phases described above. The contrast enhancement information analysis unit 21 stores the contrast enhancement information in a memory of the workstation 3.

The ROI setting unit 22 receives setting of the region of interest inputted through operation of one of the input devices such as the mouse, in the image displayed in a predetermined area of the display of the workstation 3 (hereinafter referred to as the first search target image), and finds the position information on the region of interest and a portion of the image information set corresponding to the region, in order to store the position information and the portion of the image information set in the memory of the workstation 3.

Using the position information on the region of interest and the image data set of a second search target image inputted thereto, the ROI reflecting unit 23 sets a region of interest at the inputted position in the inputted image data set of the second search target image, and finds the position information on the region of interest having been set and a portion of the image information set corresponding to the region, in order to store the position information and the portion of the image information set in the memory of the workstation 3.

The characteristic quantity calculation unit 24 carries out image analysis processing on the inputted image data sets (the portions of the image information sets corresponding to the region of interest) of the first and second search target images, and calculates a characteristic quantity thereof. Examples of the characteristic quantity include a position and a size (diameter) of an abnormal shadow in the region of interest, a luminance histogram thereof, and shape information and texture information of a lesion in the region of interest obtained by an AAM (Active Appearance Models) method (T. F. Cootes et al., "Active Appearance Models", Proc. $5^{th}$ European Conference on Computer Vision, vol. 2, pp. 484-498, Springer, 1998). The characteristic quantity may be a combination of a plurality of types of characteristic quantities.

Using the contrast enhancement information and information on the characteristic quantity of the first search target image inputted thereto, the first similar case information search unit 25 obtains a corresponding portion of the similar case information sets whose contrast enhancement information agrees with the inputted contrast enhancement information and whose characteristic quantity is different from the inputted characteristic quantity by a predetermined threshold value or smaller, from the similar case database 9.

Using the portion of the similar case information sets obtained by the first similar case information search unit 25 and the contrast enhancement information of the second search target image inputted thereto, the second similar case information search unit 26 obtains a corresponding portion of the similar case information sets whose examination ID is the same as the inputted similar case information sets and whose contrast enhancement information agrees with the inputted contrast enhancement information, from the similar case database 9.

Using the portion of the similar case information sets (hereinafter referred to as the similar case information sets A) obtained by the first similar case information search unit 25, the portion of the similar case information sets (hereinafter referred to as the similar case information sets B) obtained by the second similar case information search unit 25, and the characteristic quantity of the region of interest in the second search target image inputted thereto, the judgment unit 27 judges a degree of conformity of each of the similar case information sets with search conditions. More specifically, the judgment unit 27 judges that a portion of the similar case information sets B has a highest degree of conformity if the portion has the characteristic quantity whose difference from the characteristic quantity in the region of interest in the second search target image is a predetermined threshold value or smaller, that is, if the portion is the similar case information sets representing appropriate similar cases to both the first and second search target images. The judgment unit 27 then judges that a portion of the similar case information sets A from which the similar case information sets B have not been obtained, that is, the similar case information sets representing cases only similar to the first search target image has a second highest degree of conformity. The judgment unit 27 judges that a portion of the similar case information sets B has a lowest degree of conformity if the portion has the characteristic quantity whose difference from the characteristic quantity in the region of interest in the second search target image is larger than the predetermined threshold value, that is, if the portion is the similar case information sets that represent similar cases to the first search target image but do not represent appropriate similar cases to the second search target image at the same contrast enhancement phase as the second search target image in the examinations in which the similar case information sets representing the similar cases to the first search target image were obtained.

Figure 3A:
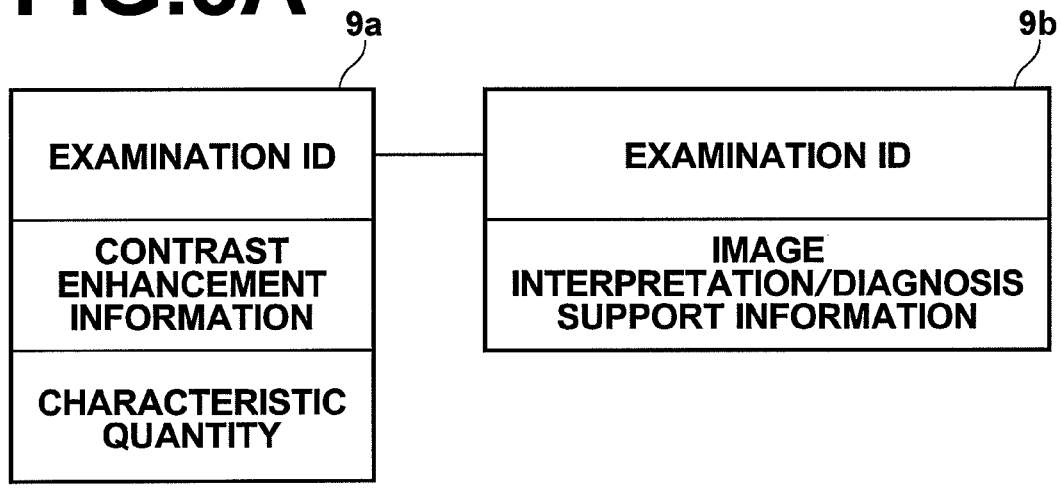
FIGS. 3A and 3B show examples of a similar case database in the embodiment.
Figure 3B:
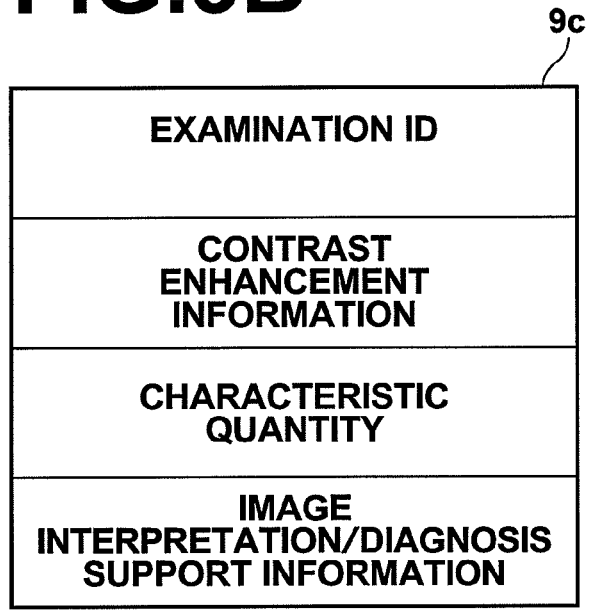

FIGS. 3A and 3B show examples of the configuration of the database 9. The similar case database 9 stores the similar case information sets each including the examination ID that identifies the examination in which the corresponding medical image that can be a similar case image was obtained, the contrast enhancement information (contrast enhancement phases) of the image, the characteristic quantity of the region of interest in the image, and the image interpretation/diagnosis support information including the image interpretation result on the image and finally confirmed diagnosis information based on the image.

In the example shown in FIG. 3A, the similar case database 9 comprises a characteristic quantity table $9a$ storing the characteristic quantity corresponding to each of the examination IDs and to the contrast enhancement information representing each of the phases and an image interpretation/diagnosis support information table $9b$ storing the image interpretation/diagnosis support information corresponding to each of the examination IDs. The tables $9a$ and $9b$ are related to each other by the examination IDs. This structure can be preferably adopted for the case where the images that can represent similar cases exist for each of the contrast enhancement phases but the image interpretation/diagnosis support information exists for each of the examinations.

In the example shown in FIG. 3B, the similar case database 9 comprises only a similar case information table $9c$ storing the characteristic quantity of the region of interest in each of the images that can represent a similar case and the image interpretation/diagnosis support information, for each of the examination IDs and the contrast enhancement information representing each of the phases. This structure is preferably adopted for the case where the image interpretation/diagnosis support information exists for each of the images that can represent a similar case. More specifically, the case refers to the case where the image itself that can represent a similar case is registered as a portion of the image interpretation/diagnosis support information.

Each of the processing units is appropriately distributed according to various performance requisites such as performance of the workstations 3, the similar case search server 8, and the network 19, the number of the workstations 3, frequency of access to the similar case search server 8, and response time. For example, the contrast enhancement information analysis unit 21, the ROI setting unit 22, the ROI reflecting unit 23, the characteristic quantity calculation unit 24, and the judgment unit 27 may be installed in each of the workstations 3 while the first similar case information search unit 25 and the second similar case information search unit 26 may be installed in the similar case search server 8. Alternatively, the contrast enhancement information analysis unit 21, the ROI setting unit 22, the ROI reflecting unit 23, and the judgment unit 27 may be installed in each of the workstations 3 while the characteristic quantity calculation unit 24, the first similar case information search unit 25, and the second similar case information search unit 26 may be installed in the similar case search server 8.

Procedures of the similar case search processing will be described below in detail by use of the flow chart in FIG. 4, the data flow in the block diagram in FIG. 2, and the database structures shown in FIGS. 3A and 3B.

User authentication of a physician to perform imaging diagnosis is carried out on the workstation 3 according to user ID and password, or biometric information such as a fingerprint, to access the medical information system. After the user authentication has been successfully carried out, an examination (interpretation) target image list is displayed on the display based on an imaging diagnosis order issued by an ordering system. The physician selects interpretation target images $I_1$ and $I_2$ from the image list by use of any one of the input devices such as the mouse. Let the image $I_1$ and the image $I_2$ be an early phase image obtained by CT by the modality 1 with infusion of a contrast material to a patient and a pre-contrast phase image obtained in the same examination, respectively. The workstation 3 requests viewing from the image information management server 4 by using the image IDs of the selected images $I_1$ and $I_2$ as search keys. The image information management server 4 having received the request searches the image information database 5 for image files (also referred to as $I_1$ and $I_2$ for the sake of simpler description) of the interpretation target images $I_1$ and $I_2$. The image information management server 4 sends the image files $I_1$ and $I_2$ to the workstation 3 that sent the request. The workstation 3 receives the image files $I_1$ and $I_2$ (#1).

The contrast enhancement information analysis unit 21 analyses the accompanying information of the image files $I_1$ and $I_2$, and obtains contrast enhancement information $P_a$ and $P_b$ of the respective images (#2).

The workstation 3 displays the images $I_1$ and $I_2$ on the display based on the image data sets of the image files $I_1$ and $I_2$, and also displays the contrast enhancement information $P_a$ and $P_b$ obtained by the contrast enhancement information analysis unit 21 at positions that can be related to the images $I_1$ and $I_2$ (#3). FIG. 5A shows an example of display of the image $I_1$ while FIG. 5B shows an example of display of the image $I_2$. Although not shown, the contrast enhancement information $P_a$ and $P_b$ (early phase and pre-contrast phase) is also displayed at the bottom of the corresponding images, for example.

The physician observes the images $I_1$ and $I_2$ displayed on the display. In the case where the physician has found a region (a cross-hatched area in FIG. 5A) that is suspicious to be a tumor in the center left of the image $I_1$, the physician marks the region by use of the mouse or the like. The ROI setting unit 22 identifies the position information and the corresponding portion of the image information set of the region marked by the operation of the mouse or the like, and stores the position information and the portion of the information set as an information set $R_1$ on the region of interest (hereinafter referred to as the ROI information) in the memory of the workstation 3 (#4).

When the physician selects "similar case search" by menu selection from a user interface displayed on the display with the mouse or the like, the workstation 3 detects the selected event corresponding to the "similar case search" item in the menu (#5; YES), and carries out the similar case search processing that will be described later. In the case where another one of items has been selected, the selected processing is carried out (#5; NO).

In the case where the "similar case search" has been selected (#5; YES), the characteristic quantity calculation unit 24 carries out the image analysis processing based on the ROI information $R_1$, and calculates a characteristic quantity $C_1$ (#8).

The first similar case information search unit 25 searches the similar case database 9 by using the calculated characteristic quantity $C_1$ and the contrast enhancement information $P_a$ as search keys, and obtains similar case information sets $A_1$, $A_2$, $A_3$, and $A_4$ at the same contrast enhancement phase as the image $I_1$ and having a content-based characteristic similar to the ROI information $R_1$ of the image $I_1$ (#9, #10; YES).

More specifically, in the case where the similar case database 9 has the structure shown in FIG. 3A, for example, the first similar case information search unit 25 accesses the characteristic quantity table 9a and sequentially compares the contrast enhancement information of each of records in the table 9a with the contrast enhancement information $P_a$. In the case where the both agree, the first similar case information search unit 25 obtains the characteristic quantity of the corresponding record. The similar case information search unit 25 then finds the difference between the characteristic quantity $C_1$ and the characteristic quantity of the record. In the case where the difference is the predetermined threshold value or smaller, the first similar case information search unit 25 judges that the region of interest of the image $I_1$ is similar to the region of interest in the image corresponding to the similar case information set, and accesses the image interpretation/diagnosis support information table 9b by using the examination ID of the record as a search key. The first similar case information search unit 25 obtains the image interpretation/diagnosis support information related to the examination ID. In this manner, the similar case information sets A1, A2, A3, and A4 each including at least the examination ID and the image interpretation/diagnosis support information and preferably including the characteristic quantity can be obtained.

In the case where no records having the same contrast enhancement information as the image $I_1$ have been found in the characteristic quantity table 9a or in the case where the records having the same contrast enhancement information as the image $I_1$ exist in the table 9a but the difference between the characteristic quantity $C_1$ and the characteristic quantity of each of the records is larger than the predetermined threshold value, the first similar case information search unit 25 judges that no similar case information sets corresponding to the image $I_1$ exist in the similar case database 9 (#10; NO), and displays a message "NO SIMILAR CASES" on the display of the workstation 3 (#14).

The second similar case information search unit 26 obtains the examination IDs of the similar case information sets $A_1$ to $A_4$, and obtains similar case information sets $B_1$ and $B_2$ having the same examination IDs as the examination IDs of the similar case information sets $A_1$ to $A_4$ and having the same contrast enhancement information as the contrast enhancement information $P_b$ of the image $I_2$ from the similar case database 9 (#11).

More specifically, in the case where the similar case database 9 has the structure shown in FIG. 3A, the second similar case information search unit 26 accesses the characteristic quantity table 9a, and sequentially compares each of the examination IDs of the similar case information sets $A_1$ to $A_4$ with the examination ID of each of the records in the table 9a. In the case where the both agree, the second similar case information search unit 26 compares the contrast enhancement information $P_b$ with the contrast enhancement information in the table. In the case where the both agree, the second similar case information search unit 26 obtains the characteristic quantity of the record, and accesses the image interpretation/diagnosis support information table 9b by using the examination ID of the record as a search key. The second similar case information search unit 26 then obtains the image interpretation/diagnosis support information related to the examination ID. In this manner, the second similar case information search unit 26 obtains the similar case information sets $B_1$ and $B_2$ having at least the characteristic quantity and the image interpretation/diagnosis support information. In this example, assume that the similar case information sets $A_1$ and $B_1$ have the same examination ID while the similar case information sets $A_2$ and $B_2$ have the same examination ID. For the similar case information set $A_3$, a corresponding portion of the similar case information sets having the same the examination ID exists but no similar case information sets having the same contrast enhancement phase as the image $I_2$ (that is, the same contrast enhancement information as the contrast enhancement information $P_b$) have been found therefrom. For the similar case information set $A_4$, no similar case information sets having the same examination ID exist. Information representing that no similar case information sets having the same contrast enhancement information as the similar case information set $A_3$ exist and information representing that no similar case information sets having the same examination ID as the similar case information set $A_4$ exist is coded and stored in a memory, for example, and usable by the judgment unit 27 as will be described later.

In parallel to Steps #8 to #11 described above, the ROI reflecting unit 23 sets the region of interest (a region in a broken circle in FIG. 5B) at the position in the image $I_2$ corresponding to the region of interest $R_1$, by using the position information of the region of interest and the image data set of the image $I_2$. The ROI reflecting unit 23 stores the position information and the corresponding portion of the image information set as ROI information $R_2$ in the memory of the workstation 3 (#6).

The characteristic quantity calculation unit 24 then carries out the image analysis processing based on the ROI information $R_2$, and calculates a characteristic quantity $C_2$ (#7).

The judgment unit 27 judges whether the region of interest in the image $I_2$ is similar to the region of interest in each of the images corresponding to the similar case information sets $B_1$, and $B_2$, based on comparison of the characteristic quantity $C_2$ with the characteristic quantity in each of the similar case information sets $B_1$ and $B_2$. Thereafter, the judgment unit 27 judges the degree of conformity of the similar case information sets $A_1$ to $A_4$ and $B_1$, and $B_2$ with the search conditions, that is, the priority as similar cases to the images $I_1$ and $I_2$ (#12).

More specifically, the difference is found between the characteristic quantity $C_2$ and the characteristic quantity in each of the similar case information sets $B_1$ and $B_2$. In the case where the difference is the predetermined threshold value or smaller, the judgment unit 27 judges that the region of interest in the image $I_2$ is similar to the region of interest in the image corresponding to each of the similar case information sets. In this case, assume that the similar case information set $B_1$ has been judged to be "similar" while the similar case information set $B_2$ has been judged to be "dissimilar".

The judgment unit 27 further judges the degree of conformity of the similar case information sets $A_1$ to $A_4$ and $B_1$ and $B_2$ with the search conditions, that is, the priority as the similar cases to the images $I_1$ and $I_2$. FIG. 6 shows an example of judgment on the degree of conformity, and shows results of judgment on the similarity of the content-based characteristic to the search target images $I_1$ and $I_2$ at the contrast enhancement phases $P_a$ and $P_b$, for each of the examination IDs of the respective similar case information sets $A_1$ to $A_4$ and $B_1$ and $B_2$. Assume that the examination IDs of the similar case information sets $A_1$ ($B_1$), $A_2$ ($B_2$), $A_3$, and $A_4$ are "001", "002", "003", and "004", respectively. In this example, the judgment unit 27 judges that the similar case information set $A_1$ ($B_1$) having the examination ID "001" and having the similar content-based characteristic at the phases $P_a$ and $P_b$ has the highest degree of conformity (that is, priority "1"). The judgment unit 27 judges that the similar case information set $A_3$ having the examination ID "003" and having the similar content-based characteristic at the phase $P_a$ but leading to no similar case information sets at the phase $P_b$ has the second-highest degree of conformity (priority "2"). The judgment unit 27 also judges that the similar case information set $A_4$ having the examination ID "004" and having the similar content-based characteristic at the phase $P_a$ but leading to no similar case information sets (at the other contrast enhancement phase) of the same examination ID has a third highest degree of conformity (priority "3"). The judgment unit 27 further judges that the similar case information set $A_2$ ($B_2$) having the examination ID "002" and having the similar content-based characteristic at the phase $P_a$ but having no similar content-based characteristic at the phase $P_b$ has the lowest degree of conformity (priority "4"). The similar case information sets having the examination ID "002" are judged to have the lower degree of conformity than for the examination IDs "003" and "004", since changes in the content-based characteristic associated with the time elapsed after infusion of a contrast material are judged to be different in the region of interest between the examination in which the images $I_1$ and $I_2$ were obtained and the examination represented by the examination ID "002", based on the results of judgment on similarity at the respective phases. Therefore, the case of the examination ID "002" can be judged affirmatively to show lower similarity than the cases of the examination IDs "003" and "004" having no similar case information set for one of the phases ($P_b$) and thus enabling no such judgment. The similar case information set having the examination ID "003" is judged to have the higher degree of conformity than the similar case information set having the examination ID "004", since the case of the examination ID "003" has no similar case information set at the phase $P_b$ alone but the similar case information set at another one of the phases in the same examination exists. Therefore, once the similar case information sets of the examination ID "003" are obtained, the similar case information sets are judged to have higher utility value than the case of the examination ID "004" that has no similar case information set at another contrast enhancement phase in the same examination. In the case where the similar case information sets having the same priority but different examination IDs exist, the degree of conformity is judged to be higher if the difference in the characteristic quantity at the contrast enhancement phase $P_a$ is smaller.

The result of the similar case search is finally displayed on the display of the workstation 3 (#13). A list of the similar case information sets with the priority thereof may be displayed as shown in FIG. 6. Alternatively, a list of the similar case information sets sorted in order of the priority may be displayed. When the physician selects a desired one of the examination IDs from the list, the image interpretation/diagnosis support information related to the examination ID is displayed. Alternatively, the image interpretation/diagnosis support information related to the examination ID having the highest priority may be displayed, instead of the list.

As has been described above, in the similar case search apparatus in this embodiment of the present invention, the contrast enhancement information analysis unit 21 obtains the contrast enhancement information (the contrast enhancement phases) $P_a$ and $P_b$ of the respective search target images $I_1$ and $I_2$ from the accompanying information of the images obtained at the different contrast enhancement phases in the same examination, and the similar case database 9 storing the similar case information sets each including the examination ID, the contrast enhancement information, the characteristic quantity, and the image interpretation/diagnosis support information is searched in the processing by the first similar case information search unit 25, the second similar case information search unit 26, and the judgment unit 27, for obtaining the similar case information sets satisfying the three search conditions comprising agreement of the contrast enhancement phases with the search target images, agreement of the examination ID between the similar case information sets, and similarity of the content-based characteristic to the search target images. Therefore, by effectively using the images at the different contrast enhancement phases in the same examination, which have not conventionally been used, accuracy of the search for similar cases improves. Therefore, this improvement contributes to reduction in errors in judgment at the time of image interpretation or diagnosis, such as erroneous judgment caused by incapability to detect a difference of a lesion from veins.

For example, as has been described above, in an examination of liver tumor, an amount of absorbed X rays (CT values) in a tumor region changes in a complex manner according to the time elapsed. Therefore, detection of a tumor region has been difficult. However, in the similar case search in the present invention, by using images obtained along with the time elapsed, information on cases showing similar complex changes can be obtained. Therefore, accuracy of tumor detection by image interpretation and diagnosis can be improved.

More specifically, the first similar case information search unit 25 obtains regarding the search target image $I_1$ the similar case information sets $A_1$ to $A_4$ having the same contrast enhancement phase $P_a$ as the first search target image $I_1$ and having the characteristic quantity related to the contrast enhancement phase $P_a$ whose difference from the characteristic quantity $C_1$ of the first search target image $I_1$ is the predetermined threshold value or smaller. The second similar case information search unit 26 then obtains the similar case information sets $B_1$ and $B_2$ having the same examination IDs as the similar case information sets $A_1$ to $A_4$ and having the same contrast enhancement information as the contrast enhancement phase $P_b$ of the second search target image $I_2$, and the judgment unit 27 extracts the similar case information set $B_1$ whose characteristic quantity is different from the characteristic quantity $C_2$ of the second search target image $I_2$ by the predetermined threshold value or smaller, from the similar case information sets $B_1$ and $B_2$. Therefore, the similar case information sets as a target of judgment by the judgment unit 27 on the similarity of the content-based characteristic to the second search target image $I_2$ are limited to the information sets ($B_1$ and $B_2$) having the same examination IDs as the similar case information sets ($A_1$ to $A_4$) that satisfy the search conditions of similarity in the content-based characteristic and agreement of the contrast enhancement phase to the first search target image $I_1$. Consequently, the number of times of similarity judgment processing on the content-based characteristic, which imposes a heavy processing load, can be reduced and faster processing can be realized.

Upon judgment on the degree of conformity with the search conditions, the judgment unit 27 also lowers the degree of conformity for the case where the similar case information set corresponding to the first search target image $I_1$ exists but no similar case information set showing the similarity in the content-based characteristic corresponding to the second search target image $I_2$ exists although the similar case information set satisfying the conditions of agreement in the contrast enhancement phase and the examination ID does exist for the second search target image $I_2$ than for the case where the similar case information set corresponding to the first search target image $I_1$ exists but no similar case information set showing agreement of the contrast enhancement phase or the examination ID exists for the second search target image $I_2$. By considering the degree of conformity in this manner, the judgment unit 27 distinguishes the two cases. Therefore, the degree of conformity is lowered for the former case where the similar case information sets are not thought to represent similar cases in consideration of the time elapsed in the examination than for the latter case where the pictorial similarity deserves consideration although the time elapsed in the examination cannot be considered. Consequently, the similar case information sets can be provided in more detailed consideration, as has been described above.

In addition, instead of the medical image itself, the characteristic quantity representing the content-based characteristic of the region of interest in the medical image is registered, as the characteristic information in each of the similar case information sets stored in the similar case database 9. Therefore, the characteristic quantity does not need to be calculated at the time of search by the first similar case information search unit 25 and at the time of judgment by the judgment unit 27. Consequently, a processing load can be reduced.

Moreover, the ROI setting unit 22 obtains the information $R_1$ and $R_2$ of the regions of interest as important parts in the corresponding images, and the first similar case information search unit 25 and the judgment unit 27 judge the similarity of the content-based characteristic for the more important parts. Consequently, more appropriate similar cases can be searched for, which contributes to improvement in accuracy of image interpretation/diagnosis.

A modification to the embodiment described above will be described next.

Figure 7:
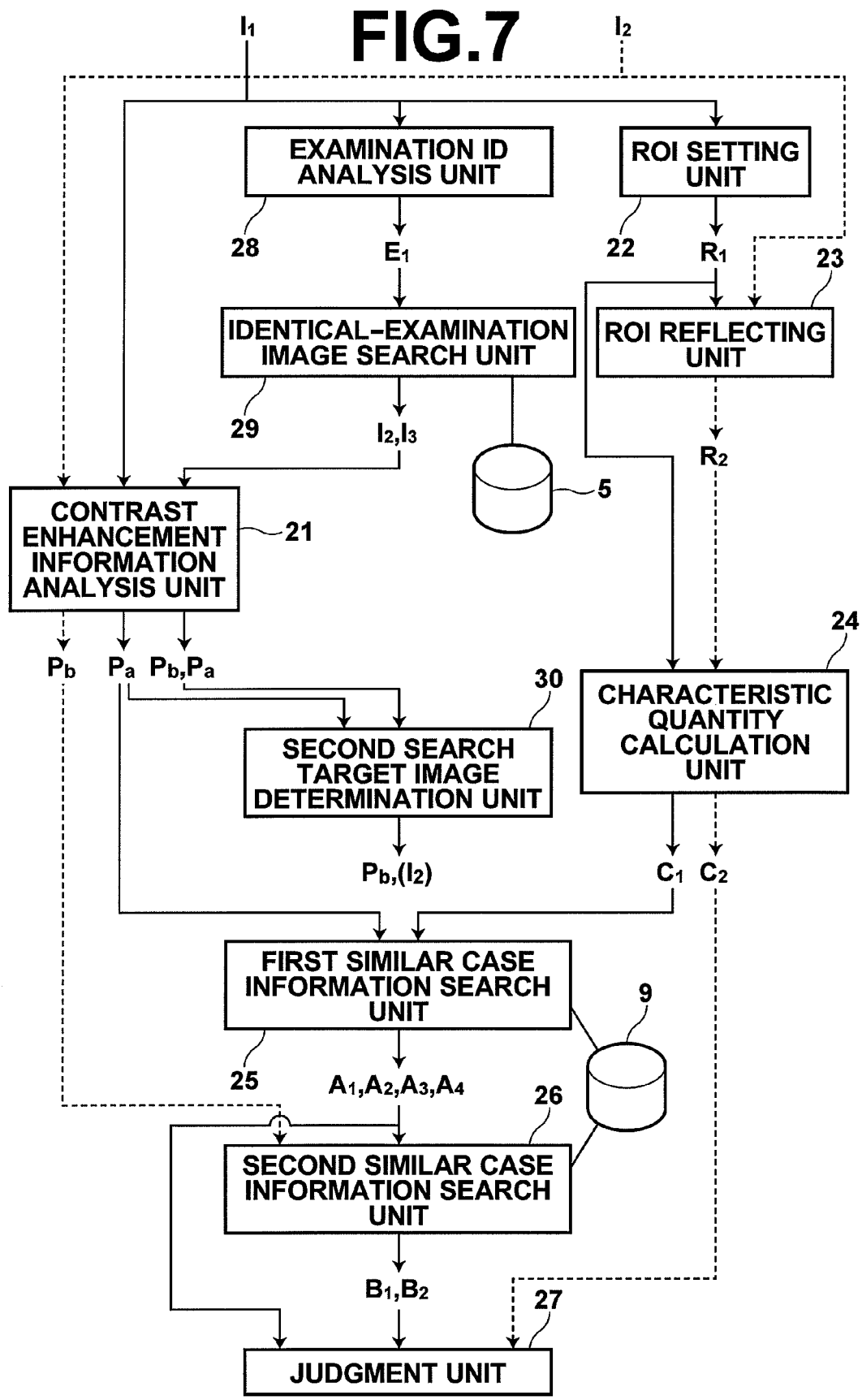
FIG. 7 is a block diagram showing the configuration of a similar case search apparatus as a modification to the embodiment.

In the above embodiment, the physician observes the images $I_1$ and $I_2$ as the interpretation targets at the different contrast enhancement phases displayed on the display of the workstation 3. However, even in the case where the physician obtains and displays only either one of the images (the image $I_1$, for example) for observation thereof, similar case search including the image obtained at the different contrast enhancement phase in the same examination as the displayed image can be considered. FIG. 7 is a block diagram showing the configuration of a similar case search apparatus realizing such similar case search. As shown in FIG. 7, the apparatus comprises an examination ID analysis unit 28, an identical-examination image search unit 29, and a second search target image determination unit 30, in addition to the configuration of the above embodiment shown in FIG. 2.

The examination ID analysis unit 28 analyses general examination information as a part of the accompanying information of the medical image data set conformed to the DICOM standard having been inputted thereto, and obtains the examination ID. The examination ID analysis unit 28 stores the examination ID in the memory of the workstation 3.

The identical-examination image search unit 29 is installed in the workstations 3, the image information management server 4, and the image information database 5. More specifically, the identical-examination image search unit 29 carries out the following procedures. The workstation 3 requests viewing from the image information management server 4 by using the examination ID inputted thereto as a search key, and the image information management server 4 having received this request searches the image information database 5 for obtaining files of images related to the same examination ID as the inputted examination ID, that is, the images as candidates for the second search target image. The image information management server 4 sends the image files to the workstation 3 that sent the request, and the workstation 3 receives the image files.

The second search target image determination unit 30 determines one of the images at the contrast enhancement phase different from the first search target image as the second search target image, by using the contrast enhancement information of the first search target image and the contrast enhancement information of the candidate images for the second search target image.

Figure 4:
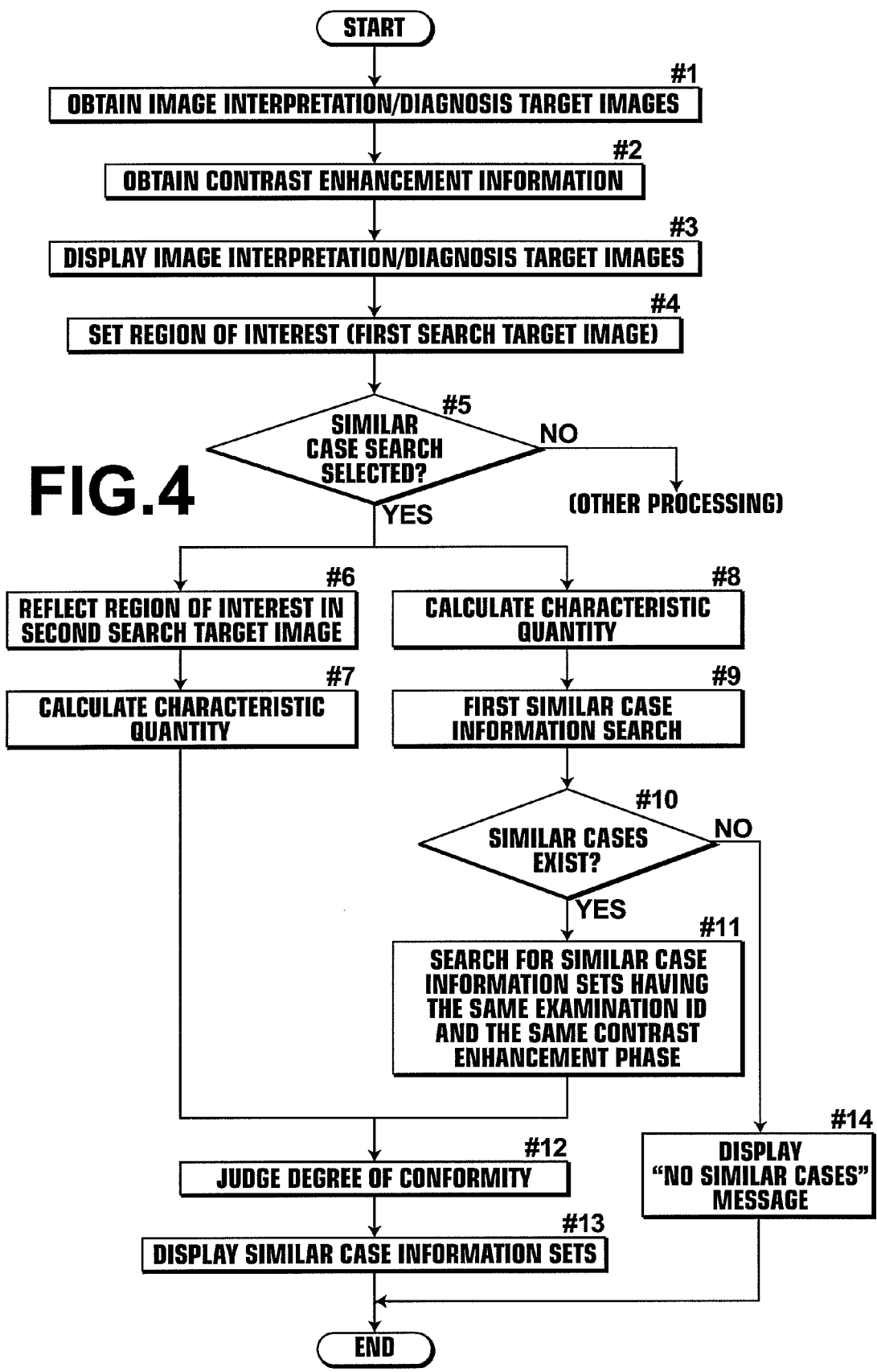
FIG. 4 is a flow chart showing procedures of similar case search processing in the embodiment.

In the above configuration including the units 28 to 30, the following procedures are carried out between Steps #5 and #6 in FIG. 4. After selection of the item "similar case search" (#5; YES), the examination ID analysis unit 28 analyses the accompanying information of the image $I_1$ and obtains an examination ID $E_1$ thereof. The identical-examination image search unit 29 searches the image information database 5 by using the examination ID $E_1$ as the search key, and obtains images $I_2$ and $I_3$ obtained in the same examination as the image $I_1$. The contrast enhancement information analysis unit 21 analyses the accompanying information of the files of the images $I_2$ and $I_3$, and obtains the information of the contrast enhancement phases $P_b$ and $P_a$ of the respective images. The second search target image determination unit 30 compares the contrast enhancement phase $P_a$ of the image $I_1$ as the first search target image with the contrast enhancement phases $P_b$ and $P_a$ of the images $I_2$ and $I_3$ obtained by the identical-examination image search unit 29, and determines the image $I_2$ having the different contrast enhancement phase as the second search target image. At Step #6 in FIG. 4, the second search target image $I_2$ determined by the second search target image determination unit 30 is used as a target of processing by the ROI reflecting unit 23. The procedures other than the procedures described above are the same as the above embodiment.

In this manner, even in the case where a medical image observer recognizes only the first search target image $I_1$, the similar case search including the second search target image $I_2$ at the different contrast enhancement phase in the same examination as the first search target image $I_1$ can be realized. Consequently, accuracy of image interpretation and diagnosis improves.

In the above embodiment, when the judgment unit 27 judges the similarity of the content-based characteristic by using the difference between the characteristic quantity in each of the similar case information sets $B_1$ and $B_2$ and the characteristic quantity $C_2$ of the second search target image $I_2$, differences in the characteristic quantity may be found between the similar case information set $B_1$ and the similar case information set $A_1$ having the same examination ID as the similar case information set $B_1$ and between the similar case information set $B_2$ and the similar case information set $A_2$ having the same examination ID as the information set $B_2$ (denoted by $\Delta_1$ and $\Delta_2$, respectively). In this case, a difference is found between the characteristic quantities $C_1$ and $C_2$ of the first search target image $I_1$ and the second search target image $I_2$ (denoted by $\Delta_0$), and the content-based characteristic is judged to be "similar" in the case where a difference between these differences (that is, $\Delta_0$-$\Delta_1$ and $\Delta_0$-$\Delta_2$) is a predetermined threshold value or smaller. In this case, the similarity can be judged by more strongly reflecting a change in the images at the different contrast enhancement phases, which improves accuracy of the search.

In the case where a plurality of characteristic quantities are used, an overall characteristic quantity may be found by weighting values of the characteristic quantities so that the judgment can be made based on a predetermined criterion for the overall characteristic quantity. Alternatively, the values of the characteristic quantities may be used as multi-dimensional characteristic quantities so that the judgment on the similarity can be made according to a distance in a multi-dimensional space.

At the time of judgment of the similarity in the content-based characteristic, up to a predetermined number of the similar case information sets sorted in order of smaller difference of the characteristic quantity from the characteristic quantity $C_1$ in the region of interest in the search target image $I_1$ may be judged to be "similar".

In the above embodiment, the physician manually sets the region of interest in the image $I_1$ by use of the ROI setting unit 22. However, a lesion candidate region in the image $I_1$ may be automatically detected and used as the ROI information $R_1$. In this case, upon display of the image $I_1$ on the display, the detected candidate region may be displayed in an identifiable manner such as marking thereon. Alternatively, the automatic detection processing and display of a detection result may be carried out in the case where a menu item "automatic detection result display" is selected by use of the mouse or the like from the user interface displayed on the display. A method of the automatic detection may be a known method described in Japanese Unexamined Patent Publication No. 2005-198887 or 2005-246032, for example. In the case where a plurality of lesion candidate regions have been found through the automatic detection, the physician may select one of the candidate regions as the ROI information $R_1$. Alternatively, a user interface for correcting the automatically detected candidate regions may be installed. If the region of interest in the interpretation target image $I_1$ is automatically detected in this manner, a burden on the image interpreter can be reduced, and oversight of a lesion can also be reduced. Even in the case where the region of interest is manually specified as has been described above, the automatic detection processing may be combined. For example, the physician may specify a rectangular region including a lesion candidate. In this case, a region of lesion candidate is detected automatically in the specified region and used as the region of interest.

In addition, as shown in FIG. 8, the similar case database 9 may have an index table representing the contrast enhancement phases of the respective similar case information sets shown for each of the examination IDs thereof. In this case, before the processing by the first similar case information search unit 25 and the second similar case information search unit 26, the index table is searched by using the contrast enhancement phase information $P_a$ and $P_b$ of the search target images $I_1$ and $I_2$ as search keys, for screening for the examination IDs having the contrast enhancement information representing the both phases. The first similar case information search unit 25 then carries out the search on the similar case information sets having the examination IDs that have been found. In this manner, a processing load on the first similar case information search unit 25 can be reduced.

In the above embodiment, the similar case search processing using the two search target images has been described. However, the similar case search processing of the present invention can be carried out in the same manner for the case where three or more search target images at different time phases (the contrast enhancement phases) are used.

Various modifications within the scope of the present invention to the system configuration, the processing flow, the database structure, the user interface, and the like of the above embodiment are also included in the scope of the present invention. The embodiment described above is merely an example, and the description above should not be used to limit the scope of the present invention. For example, the data structure shown in FIG. 3B may be used for the similar case database 9, while the image interpretation/diagnosis support information in the table 9c may include the medical image data sets. In addition, the contrast enhancement information may be a portion of the accompanying information of each of the medical image data sets, instead of an item in the table.

What is claimed is:

1. A similar case search apparatus comprising:

a similar case database storing similar case information sets each including: examination identification information identifying an examination for obtaining a medical image; time phase information representing each of time phases in the case where a plurality of medical images at the respective time phases are obtained in the examination; characteristic information representing a content-based characteristic of at least a region in the medical image; and image interpretation/diagnosis support information for supporting interpretation of a diagnosis target image, the content-based characteristic of which is similar to the medical image, or for supporting diagnosis based on the diagnosis target image having the similar content-based characteristic, while relating the time phase information of each of the time phases to the examination identification information and relating the characteristic information to the time phase information of each of the time phases;

time phase information acquisition means for obtaining time phase information representing different time phases of a plurality of search target images obtained at the time phases in an examination, the time phase information which is obtain from accompanying information added to the respective search target images; and a similar case search processor that carries out a search of the similar case database for at least the image interpretation/diagnosis support information in a corresponding portion of the similar case information sets satisfying all of search conditions comprising: a first search condition that the time phase information representing the respective time phases of the search target images exists; a second search condition that the time phase information representing the respective time phases is related to the examination identification information representing one and the same examination; and a third search condition that the characteristic information related to the time phase information representing each of the time phases represents similarity in the content-based characteristic to at least a region in a corresponding one of the search target images at the corresponding time phase;

wherein the time phase information acquisition means obtains time phase information from accompanying information added to each of the diagnosis target images;

wherein the similar case search processor searches for similar case information sets of other cases similar to cases represented by the diagnosis target images; and wherein the similar case search processor carries out the search according to the first to third search conditions by:

obtaining a corresponding portion of the similar case information sets having the time phase information representing the time phase of a first search target image as one of the search target images and representing that the characteristic information related to the time phase information thereof shows similarity in the content-based characteristic to at least a region in the first search target image; and by extracting a corresponding portion of the similar case information sets having the time phase information representing the time phase of a second search target image different from the first search target image and showing similarity in the content-based characteristic in the characteristic information related to the time phase information to at least a region in the second search target image, from a corresponding portion of the similar case information sets having the examination identification information representing the same examination as the portion of the similar case information sets having been obtained.

2. The similar case search apparatus according to claim 1, wherein, upon judgment on the similarity of the content-based characteristic to at least a region in the second search target image, the similar case search processor extracts a corresponding portion of the similar case information sets representing that a difference in the characteristic information between the respective time phases thereof is similar to a difference in the content-based characteristic of at least a region between the first and second search target images from a corresponding portion of the similar case information sets having the examination identification information representing the same examination and having the time phase information representing the time phases of the first and second search target images.

3. The similar case search apparatus according to claim 1, wherein, upon judgment on a degree of conformity with the first to third search conditions, the similar case search processor lowers the degree of conformity in order of:

(1) the case where a corresponding portion of the similar case information sets satisfying all the first to third search conditions exists for all the search target images;

(2) the case where a corresponding portion of the similar case information sets satisfying all the first to third search conditions exists for a portion of the search target images but a corresponding portion of the similar case information sets satisfying the first or second search condition does not exist for the remaining portion of the search target images; (3) the case where a corresponding portion of the similar case information sets satisfying all the first to third search conditions exists for a portion of the search target images but a corresponding portion of the similar case information sets satisfying the third search condition does not exist for the remaining portion of the search target images although a corresponding portion of the similar case information sets satisfying the first or second search condition exists for the remaining portion of the search target images.

4. The similar case search apparatus according to claim 1, further comprising second search target image acquisition means for obtaining examination identification information identifying the examination in which a first search target image as one of the search target images was obtained and the information representing the time phase of the first search target image from the accompanying information of the first search target image and for obtaining a medical image having the accompanying information including the examination identification information representing that the medical image was obtained in the same examination as the first search target image and including the information representing the time phase different from the first search target image as a second search target image.

5. The similar case search apparatus according to claim 1, wherein
the characteristic information in each of the similar case information sets is a characteristic quantity representing the content-based characteristic of at least a region in the medical image, and the similar case search apparatus further comprises
characteristic quantity acquisition means for obtaining a characteristic quantity representing a content-based characteristic of at least a region in each of the search target images.

6. The similar case search apparatus according to claim 1, wherein
said at least a region in the medical image is a region of interest in the medical image, and the similar case search apparatus further comprises
region-of-interest setting means for setting a region of interest in each of the search target images.

7. The similar case search apparatus according to claim 6, wherein the region-of-interest setting means detects the region of interest in each of the search target images.

8. The similar case search apparatus according to claim 6, wherein the region-of-interest setting means sets the region of interest in a second search target image as one of the search target images different from a first search target image as another one of the search target images, at a position corresponding to the region of interest set in the first search target image, based on the region of interest set in the first search target image.

9. The similar case search apparatus according to claim 1 further comprising display means for displaying the image interpretation/diagnosis support information obtained by the similar case search processor.

10. A similar case search method comprising the steps of:
obtaining time phase information representing different time phases of a plurality of search target images obtained at the respective time phases in an examination, the time phase information which is obtained from accompanying information added to the respective search target images; and
searching a similar case database storing similar case information sets each including: examination identification information identifying an examination for obtaining a medical image; time phase information representing each of time phases in the case where a plurality of medical images at the respective time phases are obtained in the examination; characteristic information representing a content-based characteristic of at least a region in the medical image; and image interpretation/diagnosis support information for supporting interpretation of a diagnosis target image the content-based characteristic of which is similar to the medical image, or for supporting diagnosis based on the diagnosis target image having the similar content-based characteristic, while relating the time phase information of each of the time phases to the examination identification information and relating the characteristic information to the time phase information of each of the time phases, for at least the image interpretation/diagnosis support information in a corresponding portion of the similar case information sets satisfying all of search conditions comprising: a first search condition that the time phase information representing the respective time phases of the search target images exists; a second search condition that the time phase information representing the respective time phases is related to the examination identification information representing one and the same examination; and a third search condition that the characteristic information related to the time phase information representing each of the time phases represents similarity in the content-based characteristic to at least a region in a corresponding one of the search target images at the corresponding time phase;

wherein the obtaining time phase information comprises obtaining time phase information from accompanying information added to each of the diagnosis target images;

wherein the searching a similar case database comprises searching for similar case information sets of other cases similar to cases represented by the diagnosis target images; and wherein the searching of the similar case database comprises searching according to the first to third search conditions by:

obtaining a corresponding portion of the similar case information sets having the time phase information representing the time phase of a first search target image as one of the search target images and representing that the characteristic information related to the time phase information thereof shows similarity in the content-based characteristic to at least a region in the first search target image; and by extracting a corresponding portion of the similar case information sets having the time phase information representing the time phase of a second search target image different from the first search target image and showing similarity in the content-based characteristic in the characteristic information related to the time phase information to at least a region in the second search target image, from a corresponding portion of the similar case information sets having the examination identification information representing the same examination as the portion of the similar case information sets having been obtained.

11. A non-transitory recording medium storing a similar case search program causing a computer to execute the procedures of:

obtaining time phase information representing different time phases of a plurality of search target images obtained at the respective time phases in an examination, the time phase information which is obtained from accompanying information added to the respective search target images; and searching a similar case database storing similar case information sets each including: examination identification information identifying an examination for obtaining a medical image; time phase information representing each of time phases in the case where a plurality of medical images at the respective time phases are obtained in the examination; characteristic information representing a content-based characteristic of at least a region in the medical image; and image interpretation/diagnosis support information for supporting interpretation of a diagnosis target image the content-based characteristic of which is similar to the medical image, or for supporting diagnosis based on the diagnosis target image having the similar content-based characteristic, while relating the time phase information of each of the time phases to the examination identification information and relating the characteristic information to the time phase information of each of the time phases, for at least the image interpretation/diagnosis support information in a corresponding portion of the similar case information sets satisfying all of search conditions comprising: a first search condition that the time phase information representing the respective time phases of the search target images exists; a second search condition that the time phase information representing the respective time phases is related to the examination identification information representing one and the same examination; and a third search condition that the characteristic information related to the time phase information representing each of the time phases represents similarity in the content-based characteristic to at least a region in a corresponding one of the search target images at the corresponding time phase;

wherein the obtaining time phase information comprises obtaining time phase information from accompanying information added to each of the diagnosis target images;

wherein the searching a similar case database comprises searching for similar case information sets of other cases similar to cases represented by the diagnosis target images;

wherein the searching of the similar case database comprises searching according to the first to third search conditions by:

obtaining a corresponding portion of the similar case information sets having the time phase information representing the time phase of a first search target image as one of the search target images and representing that the characteristic information related to the time phase information thereof shows similarity in the content-based characteristic to at least a region in the first search target image; and by extracting a corresponding portion of the similar case information sets having the time phase information representing the time phase of a second search target image different from the first search target image and showing similarity in the content-based characteristic in the characteristic information related to the time phase information to at least a region in the second search target image, from a corresponding portion of the similar case information sets having the examination identification information representing the same examination as the portion of the similar case information sets having been obtained.

\* \* \* \* \*